(12) United States Patent
Granada et al.

(10) Patent No.: US 8,398,662 B2
(45) Date of Patent: Mar. 19, 2013

(54) SCORING CATHETER AND METHOD FOR TREATING DISEASED HEART VALVES

(75) Inventors: Juan F. Granada, Upper Saddle River, NJ (US); Knut Sauerteig, Pürgen/Stoffen (DE)

(73) Assignee: Bavaria Medizin Technologie GmbH, Oberpfaffenhofen (DE)

( * ) Notice: Subject to any disclaimer, the term of this patent is extended or adjusted under 35 U.S.C. 154(b) by 232 days.

(21) Appl. No.: 12/478,164

(22) Filed: Jun. 4, 2009

(65) Prior Publication Data

US 2009/0306582 A1  Dec. 10, 2009

Related U.S. Application Data

(60) Provisional application No. 61/060,183, filed on Jun. 10, 2008.

(51) Int. Cl.
*A61B 17/32* (2006.01)
(52) U.S. Cl. ........................ 606/159; 606/170
(58) Field of Classification Search .................. 606/159, 606/167, 170, 198, 200, 127, 194, 213–217; 604/22; 600/564
See application file for complete search history.

(56) References Cited

U.S. PATENT DOCUMENTS

| | | | | |
|---|---|---|---|---|
| 5,224,945 A | * | 7/1993 | Pannek, Jr. | 606/159 |
| 5,318,576 A | | 6/1994 | Plassche, Jr. et al. | |
| 5,769,871 A | * | 6/1998 | Mers Kelly et al. | 606/200 |
| 6,440,128 B1 | * | 8/2002 | Edwards et al. | 606/41 |
| 6,652,548 B2 | * | 11/2003 | Evans et al. | 606/159 |
| 6,652,549 B1 | * | 11/2003 | Welten | 606/159 |
| 7,338,463 B2 | * | 3/2008 | Vigil | 604/22 |
| 2004/0143287 A1 | | 7/2004 | Konstantino et al. | |
| 2005/0137616 A1 | * | 6/2005 | Vigil | 606/170 |
| 2005/0240212 A1 | | 10/2005 | McAuley et al. | |
| 2006/0116701 A1 | | 6/2006 | Crow | |

FOREIGN PATENT DOCUMENTS

WO  9502370 A2  1/1995

* cited by examiner

*Primary Examiner* — Kathleen Holwerda
(74) *Attorney, Agent, or Firm* — Barlow, Josephs & Holmes, Ltd.

(57) ABSTRACT

The present invention provides a valvuloplasty catheter which has a scoring element at its distal part to score stenotic, calcified heart valves in radial direction and to make the single valve flaps/leaflets work again. In addition to this, the device could comprise an attached balloon to post-dilate the valve after the scoring procedure. To reduce a future recalcification, the scoring element and/or the balloon have a pharmacologic coating on their outer surface.

27 Claims, 8 Drawing Sheets

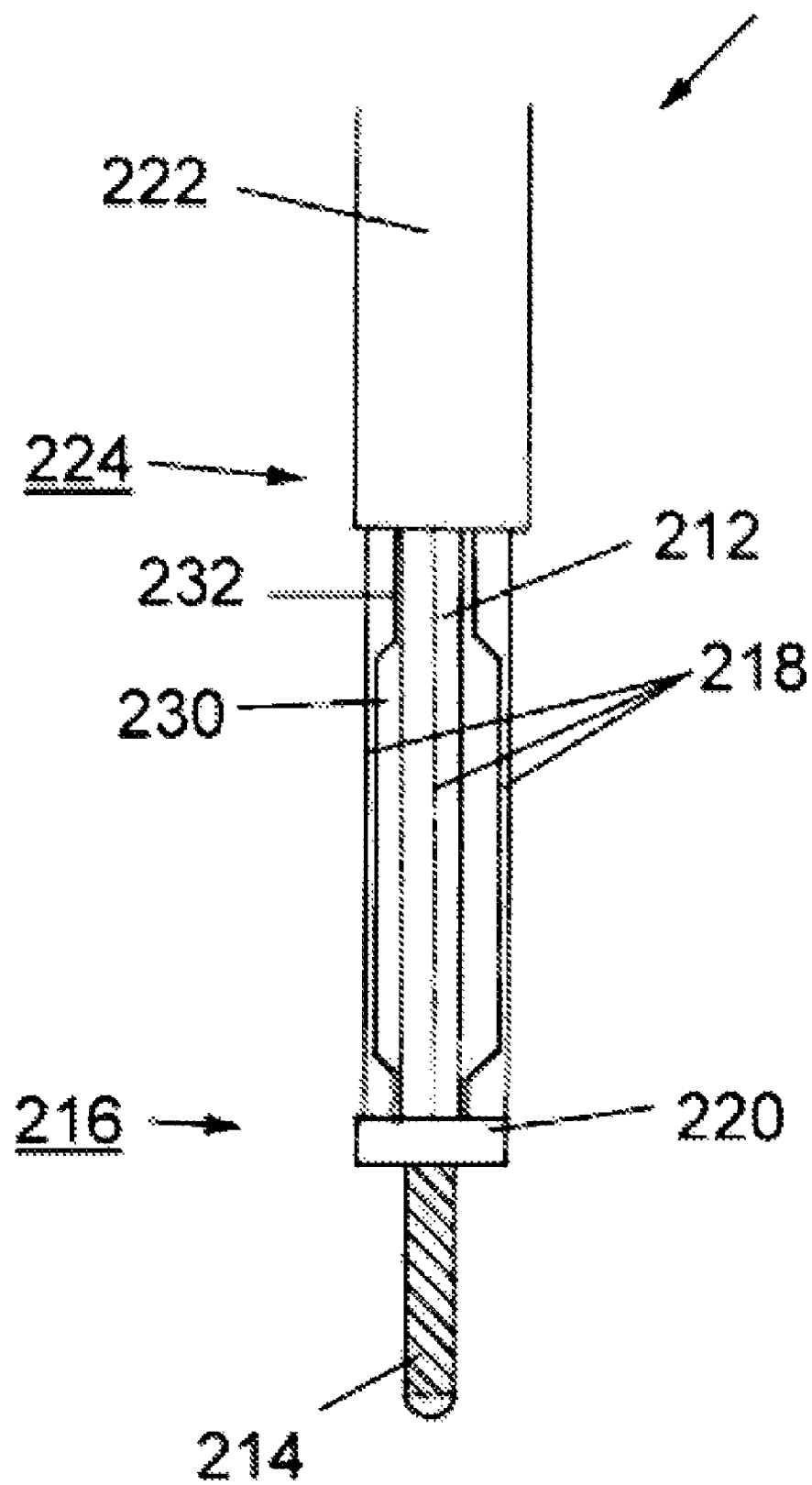

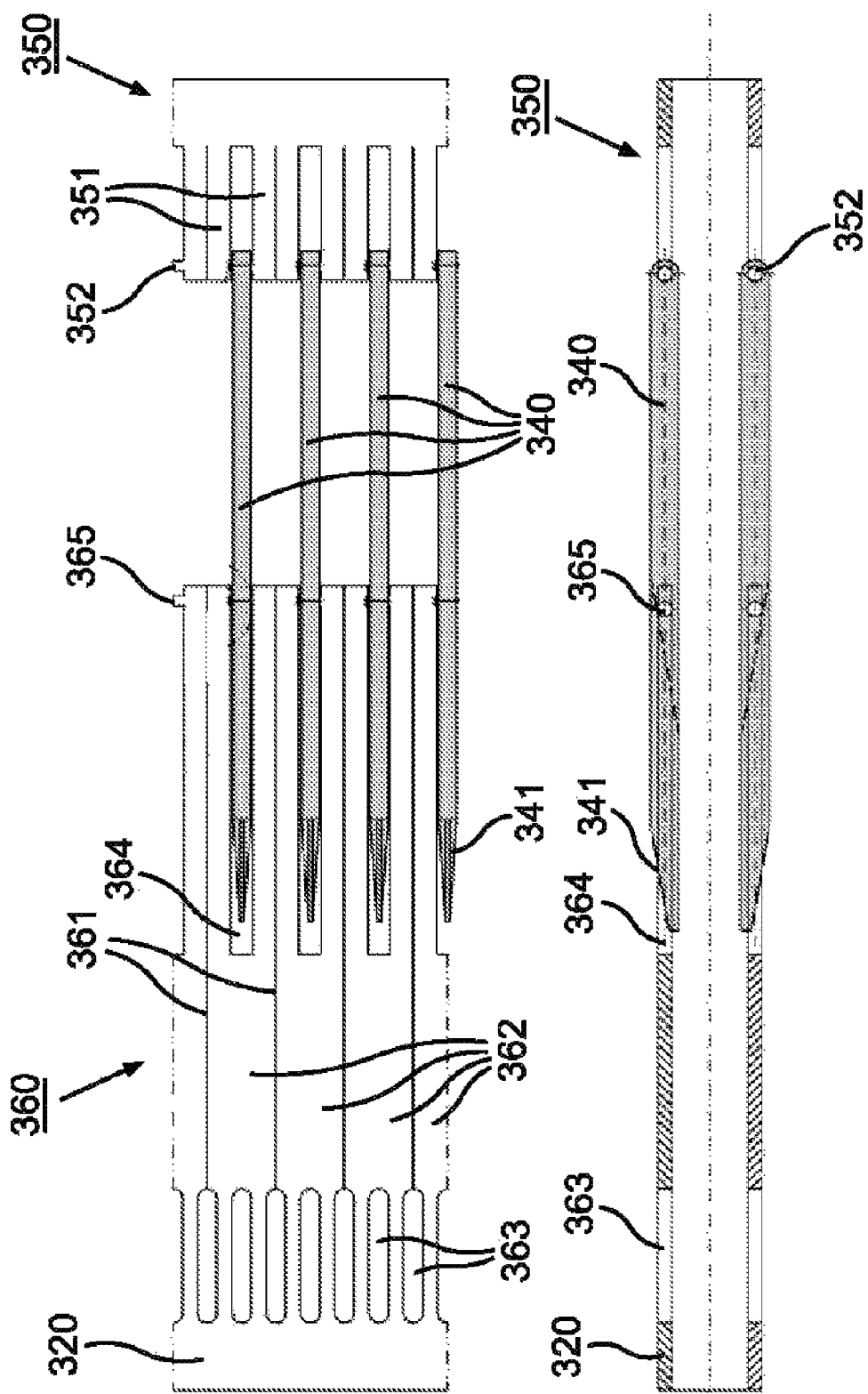

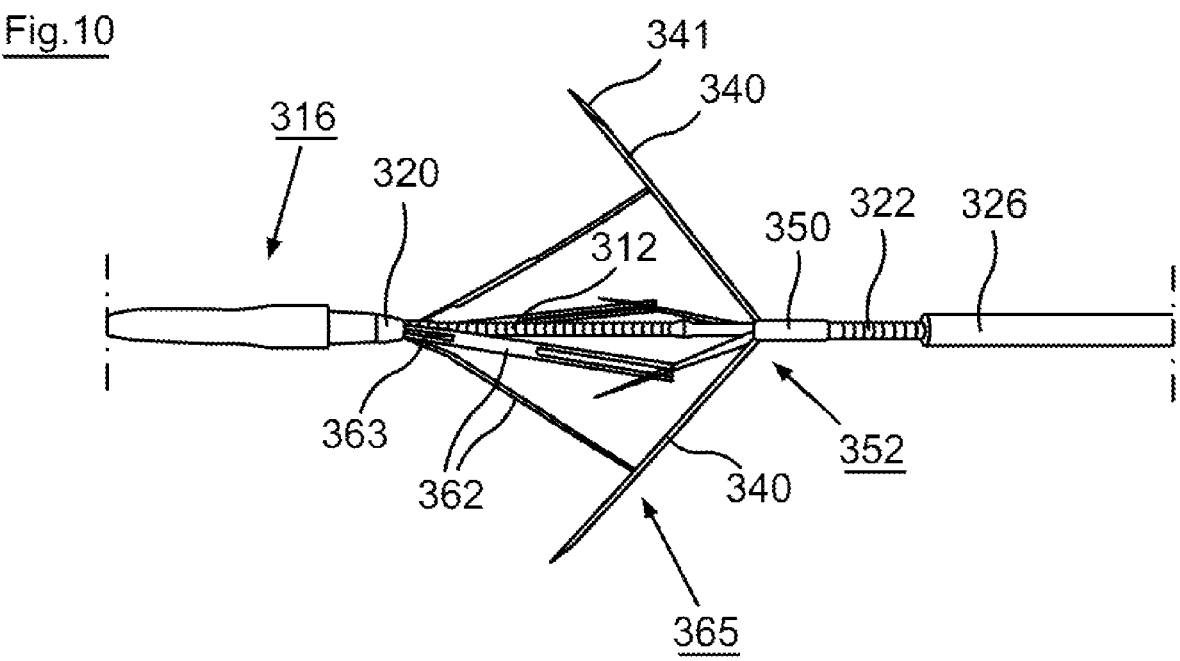

SCORING CATHETER AND METHOD FOR TREATING DISEASED HEART VALVES

CROSS REFERENCE TO RELATED APPLICATION

This application is related to and claims priority from earlier filed provisional patent application Ser. No. 61/060,183, filed Jun. 10, 2008, the entire contents thereof is incorporated herein by reference.

BACKGROUND OF THE INVENTION

Balloon valvuloplasty is a procedure in which a narrowed heart valve is mechanically stretched using a procedure that does not require open heart surgery. Balloon valvuloplasty is ineffective as it mechanically forces the dilatation of the valve by stretching the orifice. Several studies have demonstrated that the lumen gain is small and restenosis rates at 6 months are exceedingly high (70% to 90%). There are four valves in the heart, which are located either at the boundary between the atria and the ventricles (tricuspid and mitral valves) or at the exit of the heart (aortic and pulmonary valves). The valves open and close to regulate the blood flow from one chamber to the next. They are vital to the efficient functioning of the heart.

In some people the valves are too narrow (a condition called stenosis). Balloon valvuloplasty is performed on children and adults to dilate the narrowed orifice and blood flow by stretching the valve opening. It is a treatment for aortic, mitral, and pulmonary stenosis. Balloon valvuloplasty has the best results as a treatment for narrowed pulmonary valves. Results in treating narrowing of the mitral valve are generally good. It is more difficult to perform and less successful in treating narrowing of the aortic valve.

The implantation of percutaneous valves is emerging as the most promising therapy in the field of valvular heart disease. Particularly, for aortic stenosis, percutaneous aortic valve replacement has become particularly successful. There are 2 types of aortic valvular prosthesis; balloon expandable and self expandable stent based devices. In both cases, there is a critical need for precise crossing, positioning, stabilization and deployment of the device prosthesis. A particular need is effective crossing. As balloon dilation usually does not produce an effective orifice, the percutaneous valve usually encounters resistance while trying to cross the valve. A second issue is obstruction that occurs by the bulkiness of the device. In addition, positioning of the device is a critical step. Usually, interventionalists guide themselves by the "calcium shadow" created by the stiffened leaflets. A critical step during the procedure is to be able to position the prosthetic valve including partially covering the left ventricular outflow tract but avoiding the compromise of the mitral apparatus and the coronary ostia at the level of the aortic root. While the valve is deployed, stabilization is a critical step, rapid pacing is required in order to keep the valve in place during stent deployment. Therefore, there is a need for a device that releases the stiffened leaflets so the percutaneous valve can be pushed across, easily positioned in place and then deployed. In addition, device anchoring to the aortic annulus is critical. As most of these valves are based on a stented frame, device apposition with the annulus permits complete sealing and apposition avoiding undesirable para-valvular leaks, commonly seen following percutaneous valve placement and therefore reducing the short-term procedural time success and long-term efficacy of these devices.

Thus, there is a clear need in the medical community for an improved procedure for a better treatment of diseased heart valves, especially for the better treatment of heart valve stenosis. Further, there is a clear need for a corresponding medical tool to perform the improved treatment of the heart valves. In addition, there is a clear need for the development of ancillary tools that enhance the implantation and long term success of percutaneous valve devices.

SUMMARY OF THE INVENTION

The present invention provides improved medical apparatus and methods for the treatment of diseased heart valves, namely heart valves with stenosed regions. The stenosed regions will often include areas of calcified, fibrotic, or otherwise hardened tissue or other stenotic material of the type which can be difficult to dilate using conventional coronary angioplasty balloons. The methods and scoring catheters will find their greatest use in treatment of heart valve stenosis, but may also find use in treatment of the arterial, venous and/or peripheral vasculature, treatment of small vessels and/or vessel bifurcations that will not be stented, and treatment of ostial lesions. The present invention provides improved medical apparatus which are able to score a narrowed valve in an organized fashion, therefore could serve as a "stand-alone" device or primary therapy. Further it is possible to score a narrowed valve in an organized fashion, and serve as a primary therapy device if coupled with a balloon dilatation device including a drug eluting balloon. The inventive apparatus are able to serve as an ancillary device permitting better crossing for a percutaneous valve (PV) and to serve as an ancillary device permitting better control, positioning and visualization for percutaneous valve (PV) placement. Further the present apparatus are able to serve as an ancillary device permitting better valve anchoring and apposition following deployment of a percutaneous valve (PV) thus improving short term and long-term peri-valvular leaks.

In a first aspect of the present invention, a scoring catheter comprises an elongated catheter body comprising a distal end and a proximal end and at least one scoring element positioned at said distal end of the catheter body, wherein said scoring element is expandable from a contracted state when positioned near said catheter body to an expanded state with a larger diameter so that diseased heart valves can be scored and re-opened. For example the scoring element comprises at least one scoring wire, usually the scoring element comprises three to eight scoring wires. Further, it is possible that the scoring element comprises at least one cutting or dissecting edge. Typically said cutting edge is formed in parallel with the longitudinal extension of said scoring element or said scoring wire. It is also possible that multiple cutting edges are arranged in parallel with and/or in any other direction relative to the longitudinal extension of said scoring element or said scoring wire. Usually, at least a portion of said scoring element or said scoring wire has a rounded, triangular, quadrangular, trapezoidal, pentagonal, hexangular, or multi-angular profile. It is also possible that at least a portion of said scoring element or said scoring wire has a saw-like profile along its longitudinal cross-section. Alternatively, the scoring element comprises at least one scoring band.

It is believed that the inventive scoring catheter will provide improved results in the treatment of diseased heart valves. Therefore, the scoring catheter is brought through the heart valve to be treated, so that the scoring element of the catheter is positioned behind/beyond or at the level of the valve. After bringing the scoring element to said expanded state, said scoring element will be deployed or expanded at the level of said heart valve thereby scoring and re-opening said heart valve. The scoring element slits or dissects for example the calcified valve to a certain degree providing a controlled opening for the insertion of a second device such as a dilatation balloon, a percutaneous valve or other ancillary devices.

In a preferred embodiment of the present invention said scoring element or said scoring wire of said scoring catheter comprises a distal end and a proximal end, wherein said distal end of said scoring element or said scoring wire is assembled to said distal end of said catheter body, and said proximal end of said scoring element or said scoring wire is movable. For example said proximal end of said scoring element or said scoring wire is fixed to an actuating element. Usually, said actuating element could be a handle or a tube movably placed over said catheter body. Typically, said larger diameter of said scoring element is adjustable by said actuating element. Therefore it is possible to well define the diameter and the cutting angle of the scoring element which depends on the size of the heart valve to be treated and the grade of stenosis. Further it is possible that the scoring element comprises at least one marker to indicate its diameter and/or relative position in regards to the valve. For example said marker is made of a radio-opaque material. Therefore it is not only possible to adjust the target diameter of the scoring element, but also to control the expansion and location of the scoring element e.g. by way of radiological monitoring during the surgical operation.

According to further preferred embodiments of the present invention at least a portion of said scoring element or said scoring wire is covered by a movable sheath. The sheath can protect the vessels in the vicinity of the catheter against unintended cuts or injuries caused by the scoring element during introduction of the catheter into the body, in particular into the region of the heart flap to be treated. Usually said scoring element is made of a metal, a metal alloy, a polymer, a ceramic, or any combination of these materials. Usually the scoring element is made of Nitinol, stainless steel or cobalt chromium. It is further possible that at least a portion of said scoring element is physically or chemically modifiable (heat, radiation, chemical or other sources). Typically such a scoring element is heated by RF induction heating. Also, it is possible that sensors can be attached to the tip of the catheter in order to diagnose the severity of the narrowed valve as well as to improve the safety of the device by recognizing tissue contact. Also, the scoring device may be used to deliver agents to the diseased valve such as drugs, genes, viral vectors or others. According to further preferred embodiments of the present invention the scoring catheter comprises a scoring element or scoring wire which is at least partly coated or is capable of delivering drugs or compounds. Typically said drug prevents or reduces adverse and inflammatory effects and/or the restenosis of said treated heart valves. It is further possible that at least a portion of said scoring element or said scoring wire extends in a direction parallel to and/or at an angle to that of the longitudinal axis of said catheter. But it is also possible that at least a portion of said scoring element or said scoring wire is arranged helically, circumferentially, or in a serpentine pattern over said catheter body. In a further preferred embodiment of the present invention said scoring element comprises an expandable cage structure. Specifically, the cutting device could be assembled with a distal cage or centering device such as a balloon to improve the stability of the device and also serve as a guidance tool for the percutaneous aortic valve placement.

In other preferred embodiments of the present invention the scoring catheter comprises at least one expandable balloon to dilate the heart valve after a scoring procedure. For example, the balloon is positioned proximal to said scoring element. But it is also possible that said balloon is positioned within or inside said scoring element. If the balloon is positioned within said scoring element, the scoring element could be not fixed to the surface of said balloon and the scoring element and the balloon are expandable independently from each other. It is also possible that said scoring element is fixed to the surface of said balloon and the expansion of said scoring element is accomplished by the expansion of said balloon. Further it is possible that said balloon is positioned over said scoring element which means that in this case the balloon could be moved over the scoring element after the scoring of the heart valve has been accomplished. Typically, the balloon is non- or semi-compliant. It is also possible that said balloon is at least partly coated with a drug agent. Said drug usually prevents or reduces adverse and inflammatory effects and/or the restenosis of said treated heart valves. It is further possible that said balloon has a rounded, triangular, multiangular, or cube-like shape. For such an inventive catheter it is possible that after the scoring treatment the catheter is again brought through the heart valve and the balloon will be inflated to dilate the narrowed heart valve.

In a second aspect of the present invention, a method for treating diseased heart valves, the method comprises the steps of providing a scoring catheter comprising an elongated catheter body with a distal end and a proximal end and at least one scoring element positioned at said distal end of said catheter body, wherein said scoring element is expandable from a contracted state when positioned near said catheter body to an expanded state with a larger diameter; placing said scoring element in its contracted state at the level of the heart valve to be treated; expanding said scoring element to an expanded state with a larger diameter than in its contracted state; and thereby scoring and re-opening said heart valve. The mechanism of function can be pulling, retracting, pushing forward or simply opening the scoring element at the level of the narrowed valve.

In a preferred embodiment the inventive method further comprises the further step of positioning a balloon in the region of the scored heart valve and expanding the balloon to dilate the scored heart valve. It is possible that the step of expanding the scoring element includes the step of expanding a balloon which is positioned within said scoring element. It is further possible that said scoring element and/or said balloon is/are at least partly coated with a drug compound. Said drug prevents or reduces adverse and inflammatory effects and/or the restenosis of said treated heart valves. It is believed that the inventive method is most useful in treating the narrowing of the heart valves. The inventive method uses a scoring catheter as described in the above. Also the balloon can be part of the catheter, not necessarily within the scoring component.

In a third aspect of the present invention the scoring catheter as described in the above is used in a balloon valvuloplasty. Another option is to have two devices. Just the scoring catheter, that runs through a PTA catheter. The PTA catheter's specific advantage is that there is a large inner diameter of a lumen, through which the scoring catheter runs easily. The scoring catheter can be used for all diameters, but the balloon would need to fit exactly to the needed diameter of the heart valve (like an endoscope). Furthermore, safety features may be added such as a proximal protection device. E.g. an additional basket is built in to protect from distal embolization right after cutting the tissue.

BRIEF DESCRIPTION OF THE DRAWINGS

FIG. 4 is a schematic illustration of the distal portion of a scoring catheter according to a third embodiment of the invention;

FIG. 6b is a cross-sectional view of a sheath to be positioned over the scoring element of FIG. 6a;

FIG. 8 is a top view of a scoring element of a scoring catheter according to a sixth embodiment of the invention in a flat projection;

FIG. 9 is a cross-sectional view of the real form of the scoring element of FIG. 8 in a contracted state; and FIG. 10 is a schematic illustration of a scoring catheter comprising the scoring element of FIG. 9 in an expanded state.

DETAILED DESCRIPTION OF SOME PREFERRED EMBODIMENTS OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention. In the present application, the term "proximal" refers to a direction that is generally towards a physician during a medical procedure, while the term "distal" refers to a direction that is generally towards a target site within a patient's anatomy during a medical procedure.

Figure 1:
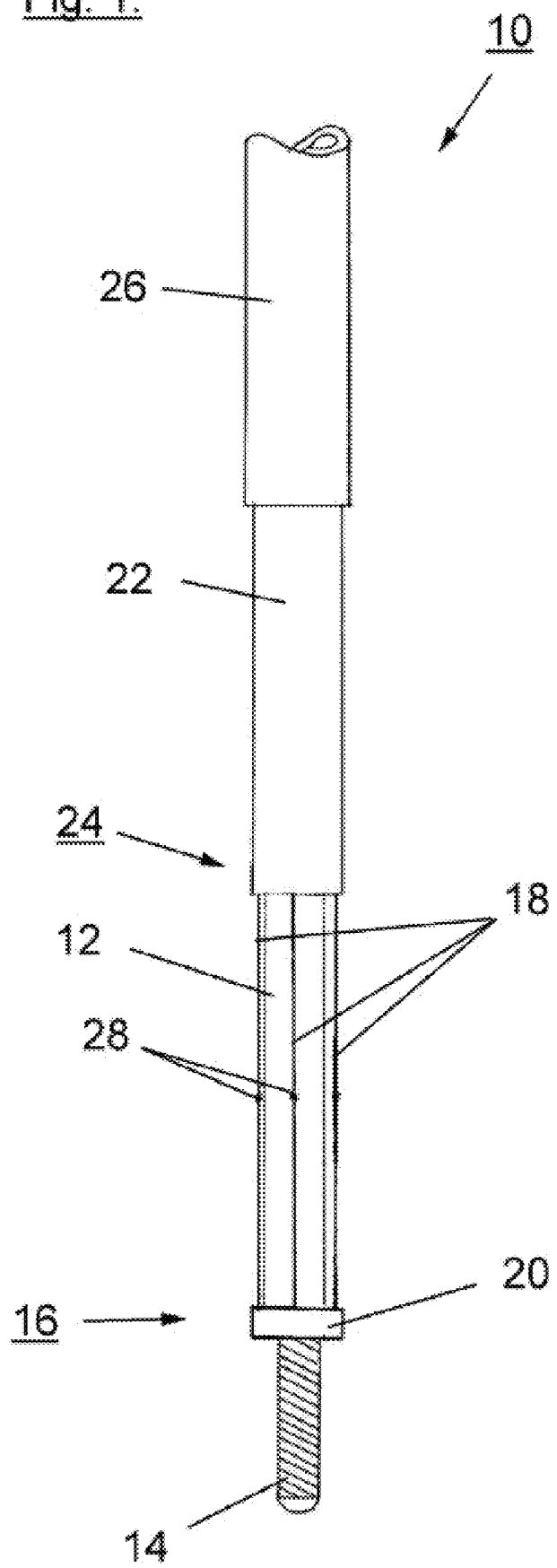
FIG. 1 is a schematic illustration of the distal portion of a scoring catheter according to a first embodiment of the invention with a scoring element in a contracted state.

Referring now to FIG. 1, scoring catheter 10 generally includes an elongated flexible catheter body 12 having a distal end 16 and a proximal end (not shown). The catheter body 12 comprises a lumen for guiding a guide wire 14. A scoring element comprising four scoring wires 18 is positioned at said distal end 16 of the catheter body 12. The scoring wires are fixed to the distal end 16 of the catheter body 12 by a connecting element 20. The proximal end of the scoring wires 18 are fixed to the distal end 24 of a tube 22. The tube 22 is movable over and along the catheter body 12 and therefore functions as a push-tube. The scoring catheter 10 according to the first embodiment as shown in FIG. 1 further comprises a sheath 26 which can be moved over the tube 22 and a scoring element comprising the scoring wires 18. FIG. 1 shows the scoring element with the scoring wires 18 in a contracted state when positioned near the catheter body 12. Further, it can be seen that according to this embodiment of the catheter 10 the scoring wires 18 extend in a direction parallel to that of the longitudinal axis of the catheter 10 or the catheter body 12. But it is also possible that at least a portion of said scoring wire is arranged helically, circumferentially, or in a serpentine pattern over said catheter body 12. It is further possible that said scoring wires 18 extend in a direction at an angle to the longitudinal axis of the catheter 10 or the catheter body 12. It can also be seen that each of the scoring wires 18 comprises a marker 28, wherein the markers 28 are made of a radio-opaque material.

Figure 2:
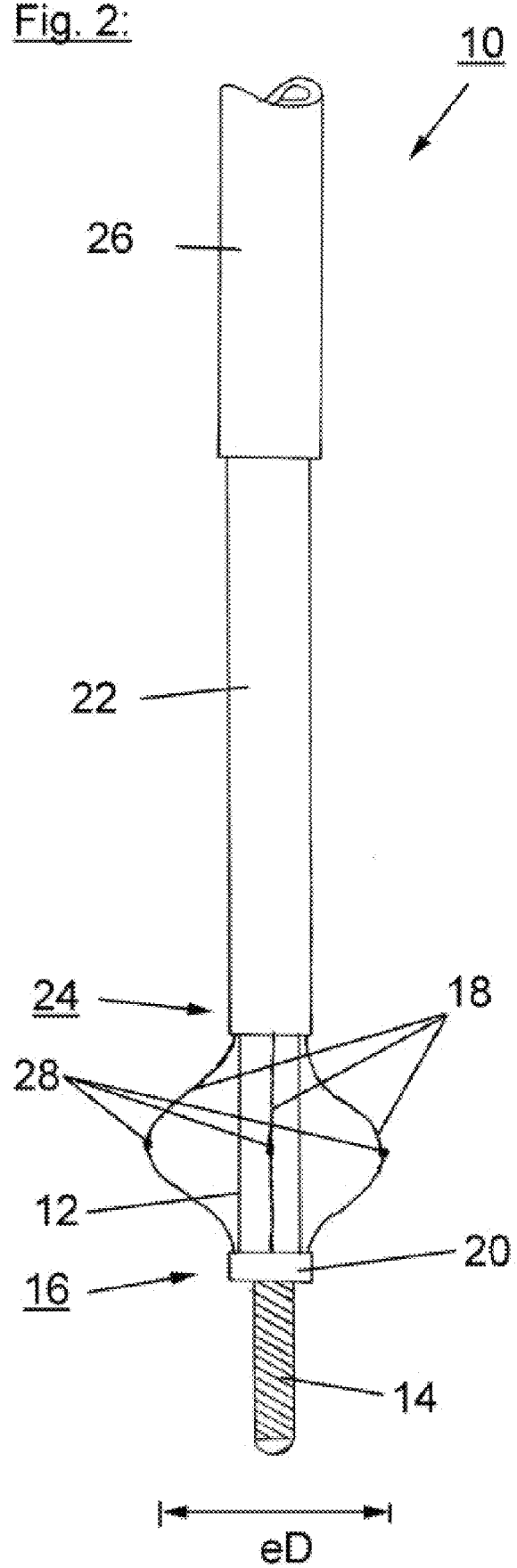
FIG. 2 is a schematic illustration of the distal portion of the scoring catheter according to FIG. 1 with said scoring element in an expanded state.

FIG. 2 schematically illustrates a distal portion of the scoring catheter 10 according to FIG. 1 with said scoring element in an expanded state. It can be seen that the scoring element comprising the scoring wires 18 has been expanded by moving the tube 22 towards the distal end 16 of the catheter body 12. The scoring element is now expanded and comprises an expanded diameter (eD). In this expanded state the scoring element with the scoring wires 18 is able to score diseased portions of a heart valve. Especially it is possible to score stenotic heart valves. As can be seen the diameter of the scoring element with the scoring wires 18 can be controlled by controlling the movement of the markers 28. This may e.g. be done by way of radiological monitoring. FIG. 2 clearly shows that pushing the tube 22 forward into a distal direction results in an expansion of the scoring wires in a radial direction.

Figure 3:
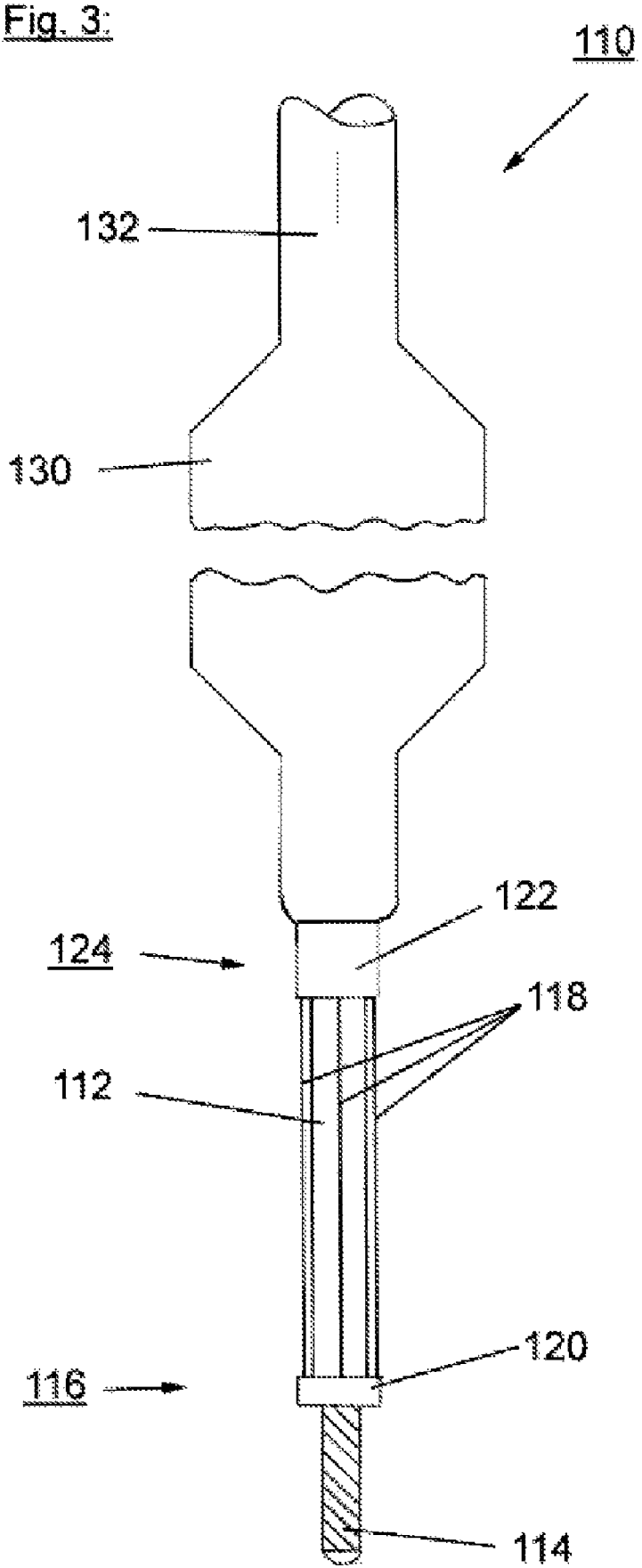
FIG. 3 is a schematic illustration of the distal portion of a scoring catheter according to a second embodiment of the invention.

Referring now to FIG. 3, a second embodiment of the scoring catheter 110 will be described. As can be seen, in this case the sheath 26 is replaced by a balloon catheter comprising a balloon 130 and a balloon tube 132. The balloon tube 132 or delivery catheter may have lumen or tubes in a coaxial or co-linear orientation with the longitudinal axis of the catheter body 112 and the pushing tube 122. The balloon catheter 132 will be used after the scoring procedure of the heart valves for post-dilatation of the scored heart valves. In the shown embodiment the distal end of the balloon catheter is fixed to the distal end 124 of the pushing tube 122. It is also possible that the balloon catheter comprising the balloon 130 and the balloon 130 is movable over the tube 122. The catheter 110 comprises a scoring element comprising four scoring wires 118. The scoring element is shown in a contracted state positioned near the catheter body 112. The distal end of the scoring element and the scoring wires 118, respectively, is/are fixed to a connecting element 120, which is positioned at the distal end 116 of the catheter body 112. The catheter body 112 comprises a lumen for guiding a guide wire 114. The balloon 130 is non- or semi-compliant. It is possible that the balloon 130 is at least partly coated with a drug agent to prevent or reduce adverse and inflammatory effects and/or the restenosis of said treated heart valves. In the embodiment as shown in FIG. 3 the balloon 130 has a rounded shape, but it is also possible that the balloon 130 has a triangular, multiangular, or cube-like shape. The balloon 130 and scoring element with the scoring wires 118 are expandable independently from each other.

Referring now to FIG. 4, a scoring catheter 210 according to a third embodiment of the invention is shown. The scoring catheter 210 comprises an elongated catheter body 212 with a distal end 216 and a proximal end (not shown). A scoring element comprising four scoring wires 218 is positioned at the distal end 216. The distal ends of the scoring wires 218 are connected to a connecting element 220 at the distal end 216 of the catheter body 212. The proximal end of the scoring wires 218 are connected to the distal end 224 of tube 222. By pushing the tube 222 into the distal direction the scoring element comprising the scoring wires 218 will be expanded. The scoring catheter 210 further comprises a balloon catheter comprising a balloon 230 and a balloon tube or delivery catheter 232. The balloon catheter is positioned between outer surface of the catheter body 212 and the inner surface of tube 222. The balloon 230 is placed under or in the scoring element. FIG. 4 shows the scoring element in a contracted state positioned near the catheter body 212. By inflating the balloon 230 scoring element with the scoring wires 218 will be expanded in a radial direction. But it is also possible to first push the tube 222 in a distal direction in order to expand the scoring element alone. After the scoring procedure the balloon 230 can be inflated to finish the treatment with postdilatation with the heart valve to be treated. As is the case with the scoring catheters described in FIGS. 1 to 3, the connecting element 220 cannot be moved, but is fixed to the distal end 218 of the catheter body 212.

Figure 5A:
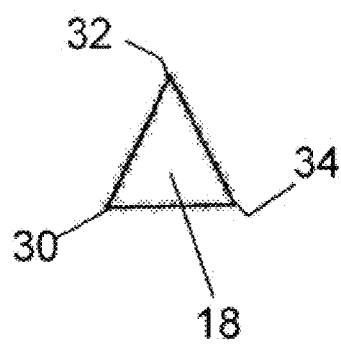
FIGS. 5a-5c schematically illustrate different profiles of the scoring element of the scoring catheter.
Figure 5B:
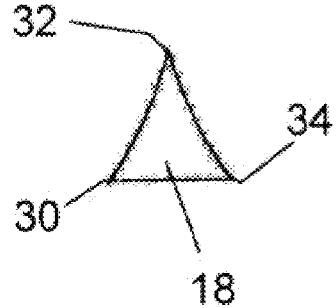
Figure 5C:
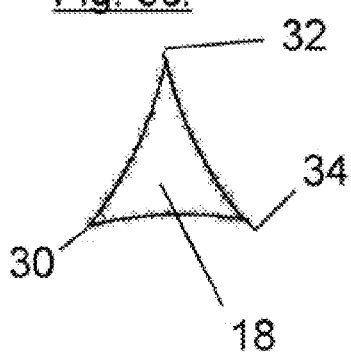

FIGS. 5a to 5c schematically illustrate different profiles of the scoring element of the scoring catheters 10, 110, 210. As can be seen from FIG. 5a, the scoring element comprises a scoring wire 18 which has a triangular profile. By having a triangular profile three cutting edges 30, 32, 34 are created. The sides of the triangles are straight. In contrast thereto, two sides of the triangular scoring wire 18 according to FIG. 5b are curved. In FIG. 5c a triangular guide wire 18 is shown wherein all three sides of the triangle are curved.

Figure 6A:
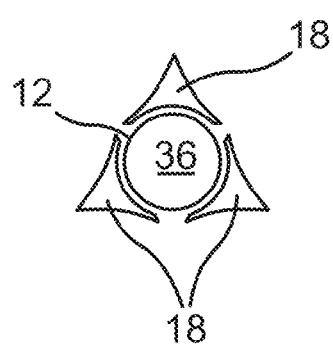
FIG. 6a is a cross-sectional view of the distal portion of a scoring element of a scoring catheter according to a fourth embodiment of the invention.

FIG. 6a is a cross-sectional view of the distal portion of a scoring element of a scoring catheter according to a fourth embodiment of the invention. It can be seen that in this embodiment three scoring wires 18, as illustrated in detail in FIG. 5c, are positioned around the catheter body 12. It can be further seen that the catheter body 12 comprises a lumen 36 for guiding a guide wire (not shown).

Figure 6B:
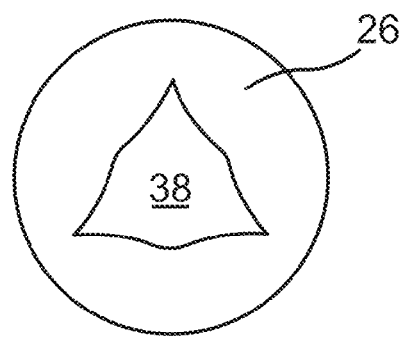

FIG. 6b is a cross-sectional view of a sheath 26 to be positioned over the scoring element comprising three scoring wires 18, as shown in FIG. 6a. The sheath 26 comprises a lumen 38 which is formed to receive the triangular scoring wires 18, as shown in FIG. 6a.

Figure 7:
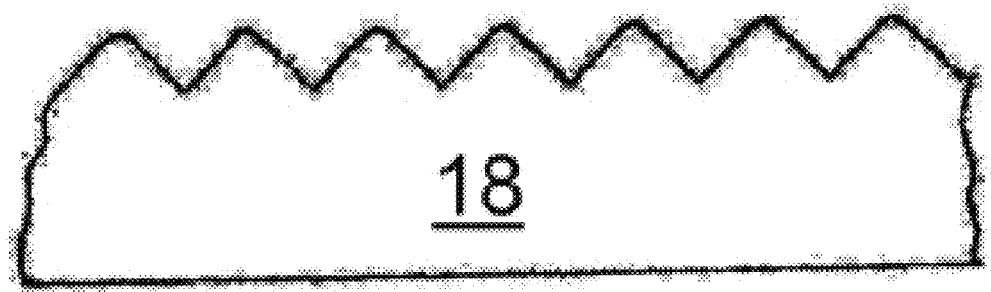
FIG. 7 is a longitudinal cross-sectional view of a scoring element of a scoring catheter according to a fifth embodiment of the invention.

Referring now to FIG. 7, a longitudinal cross-sectional view of a scoring element of a scoring catheter according to a fifth embodiment is shown. The scoring element comprises at least one scoring wire 18 having a saw-like profile, as shown in FIG. 7.

A sixth embodiment of the present invention is now explained in detail along with FIGS. 8 to 10. FIG. 8 shows a scoring element with pivotable knives 340. Each of these knives is a pivotable rodlet having a cutting edge 341 at its distal end. In the present case, the extension of the cutting edge 341 in longitudinal direction of the rod-shaped knives 340 is less than a quarter of the length of a knife 340. However, the cutting edge 341 can be longer as well. Specifically, the cutting edge can reach to an axis 365 pivoting the corresponding knife 340.

In the example of FIG. 8 a scoring element includes four knives 340. Other favourable embodiments of scoring catheters may include 3, 5, 6 and more knives. In the contracted state of the scoring element each knife 340 extends parallel to the axis of the elongated catheter body. Furthermore, each knife 340 is pivotably hinged at a proximal connecting element 350 which may be blanked from a metal sheet or may be produced from a metal tube. Additionally, each knife 340 is pivotably hinged at a spreading element 360 integrally formed with a distal connecting element 320. This distal connecting element 320 together with the spreading element 360 is also blanked from a metal sheet or produced from a metal tube. It is one single piece like the proximal connecting element 350 and supports four knives 340 in the present case.

In FIG. 8 the scoring element is illustrated as flat projection, actually, however, it is a tube as shown in FIG. 9. In the flat projection of FIG. 8 the spreading element 360 has the shape of a rectangle. It has several cuts 361 extending parallel to the knives 340 and also parallel to the longitudinal axis of the catheter body. These cuts 361 divide the spreading element 360 into four spreading rodlets 362. The cuts 361 end at a distal connecting element 320. The connecting element 320 connects the spreading rodlets 362 at the distal end of the scoring element.

At the feet of the spreading rodlets 362 there are provided a plurality of openings 363 adjacent to the connecting element 320. The function of these openings 363 is to reduce the stiffness of the spreading rodlets 362 at their foot sections.

Thus, it is possible to bend the spread rodlets 362 outwardly at their foot sections. Additionally, the function of the foot sections of the spread rodlets 362 including the openings 363 is to resiliently reset the spread rodlets 362 from a bent position (extracted state of scoring element; compare FIG. 10) into a flat position (contracted state of scoring element) as shown in FIGS. 8 and 9.

The proximal end of each spread rodlet 362 has a U-shape. I.e. there is provided an opening 364 at the proximal end of each spread rodlet 362. The opening 364 extends from the proximal end of the spread rodlet 362 roughly to the middle section of the corresponding spread rodlet in the axial direction of the catheter. Each opening 364 is adapted to receive the tip of a knife 340. This can also be seen in the cross-sectional view of FIG. 9.

At the proximal end of each spread rodlet 362 there is provided an axis 365 which serves for pivoting the corresponding knife 340 in its middle section. The axis 365 joins the end of the brackets of the U-shaped proximal end of each spread rodlet 362. The axis 365 may be integrally formed with one of these two brackets. After receiving the knife 340, the axis 365 can be welded to the other bracket.

As indicated above the tip of each knife 340 is formed by a cutting edge 341. At the opposite end the knife 340 is pivoted at the proximal connecting element 350. For this purpose brackets 351 are provided at the proximal connecting element 350. The free ends of two brackets 351 are joined with an axis 352 similar to the mounting of the knife 340 at the end of the spread element 362.

As illustrated in FIG. 9 the complete scoring element has a tubular shape. This means that the distal connecting element 320 together with the spreading element 360 on the one hand and the proximal connecting element 350 on the other hand are tubular. Both tubular elements are joined by the knives 340 only.

The function of the scoring catheter comprising pivotable rodlets like knives 340 will be discussed in the following along with FIG. 10. In this Figure the scoring catheter is shown in an expanded state whereas FIGS. 8 and 9 show the scoring element of this scoring catheter in a contracted state. The expanded state of the scoring catheter is characterized by the knives 340 pivoted outwardly. This means that the pivotable rodlets, i.e. the knives 340, are no longer parallel with the catheter body 312. This is achieved by pushing the proximal connecting element 350 to the distal connecting element 320. Thereby the spread rodlets 362 are bent outwardly at their foot sections at the openings 363.

For inserting the scoring catheter into a vessel of a patient the scoring element of the scoring catheter is moved to a contracted state where sheath 326 covers the complete scoring element and hits against the distal end 316 of the catheter. When reaching the heart valve as described above, the sheath 326 is retracted and tube 322 inside the sheath 326 is pushed forward in distal direction thereby spreading the pivotable rodlets i.e. knives 340. The spreading of the scoring element to the extracted state as shown in FIG. 10 is similar to the opening of an umbrella. After scoring the heart valve, the tube 322 together with the proximal connecting element 350 is drawn back, so that the scoring element reaches the contracted state again.

The scoring catheter includes one or more pivotable rodlets for scoring diseased heart valves, an example of which is shown in the FIGS. 8 to 10, may also include features of the embodiments described above. Specifically, the catheter of FIG. 10 may be provided with a balloon for spreading the knives 340 (i.e. the pivotable rodlets).

The catheters as shown in FIGS. 1 to 10 can be used in a method for treating diseased heart valves, the method comprising: providing a scoring catheter comprising an elongated catheter body with a distal end and a proximal end and at least one scoring element positioned at said distal end of the catheter body, wherein said scoring element is expandable from a contracted state when positioned near said catheter body to an expanded state with a larger diameter; placing said scoring element in its contracted state behind a heart valve to be treated; expanding said scoring element to an expanded state with a larger diameter than in its contracted state; and retracting said scoring element through an opening of said heart valve thereby scoring and re-opening said heart valve.

In the case that the catheter comprises a balloon catheter, the method further comprises the steps of positioning a balloon of said balloon catheter in the region of the scored heart valve and of expanding the balloon. If the balloon is positioned within the scoring element, the method could include the step of expanding said balloon which is positioned in said scoring element. In general, a physician performs said method by introducing said scoring catheter including said balloon catheter into a peripheral artery and threading the scoring catheter to the narrowed region of the heart valve. During this stage, the scoring element and the balloon is unexpanded/uninflated and collapsed onto the shaft of the catheter in order to present a low profile which may be passed through the arterial lumens and the heart valves to be treated. Once the scoring element is positioned behind the stenotic heart valve the scoring element will be expanded. Then, said scoring element will be retracted through an opening of said heart valve thereby scoring and re-opening said heart valve. After that said balloon is positioned at the scored region of the heart valve. Then, the balloon is expanded by pumping a mixture of for example, saline and contrast solution through the delivery tube/catheter of the balloon catheter to the balloon. As a result, the balloon presses against the inner walls of the scored heart valves to dilate them. After satisfactory widening of the stenosis has been achieved, the balloon is deflated and the scoring element contracted. The scoring catheter then is retracted and removed from the patient's vessel with the scoring element in the contracted state and the balloon in the deflated state.

The scoring elements or the scoring wires of the scoring catheters as described in FIGS. 1 to 10 can be at least partly coated with a drug agent which prevents or reduces adverse and inflammatory effects and/or the restenosis of said treated heart valves. It is further possible that said scoring elements comprise an expandable cage structure. Further, the proximal ends of said scoring elements or scoring wires is/are fixed to an actuating element. Said actuating element could be a handle or said tube movably placed over said catheter body. The larger diameter of said scoring element is adjustable by said actuating element. The scoring element usually is made of a metal, a metal alloy, a plastic material, a polymer, a ceramic, or any combination of these materials. Typically said scoring element is made of Nitinol or stainless steel. It is also possible that at least a portion of said scoring element is heatable, for example the scoring element is heated by RF induction heating. Usually, the outer diameter of said scoring catheters is smaller than 40 mm. For performing the described method for treating diseased heart valves it is also possible to use a scoring catheter without a balloon and thereafter to use a balloon catheter without scoring element.

Typically, the scoring catheter according to the present invention further comprises a scale at the proximal end of the pushing tube in order to control the diameter of the expanded scoring element.

The catheter bodies, pushing tubes, balloons and/or sheaths as described in FIGS. 1 to 10 may be manufactured from polyurethane, polyethylene, tetrafluoroethylene, polytetrafluoroethylene, fluorinated ethylene propylene, nylon, PEBAX, plastic material in general, silicone or the like.

The scoring catheter 10 may have further features like:
a) The device catheter may have markers allowing the positioning and alignment of the scoring elements with the stenosed aortic valve. The marker arrangement can assist in locating the boundaries of the narrowed valve thus assisting with subsequent location of the prosthetic valve.
b) The scoring element may have a pre-specified length so it is safe. The length should not exceed the size of diameter of the entire valvular ring.
c) The scoring element can open below, at or above the stenosed valve by pulling, pushing or other deployment mechanisms (screwing or step wise deployment).
d) The scoring element may have markers. Upon deployment these markers may align in different ways (i.e., parachute-like) in the inferior part of the valve providing a "marker" zone for the posterior placement of the valve. That means the device can serve as a marker or positioning tool for valve placement as well.
e) The scoring elements can be arranged in parallel but also in a wide variety of configurations such as baskets, spirals, crooked elements, etc. in order to improve cutting efficiency and safety.
f) The device may be assembled with a more proximal basket to avoid embolization of scored material.
g) The device may be assembled with a balloon to permit valve dilation.
h) The device may be assembled with a stabilizing device permitting centering and more stability of the cutting elements.

The scoring element's deployment angle and length of cutting can be determined or pre-set using the device's features.

It will be appreciated by persons skilled in the art that the present invention is not limited to what has been particularly shown and described hereinabove. Alternate embodiments are contemplated that fall within the scope of the invention.

We claim:
1. A scoring catheter comprising:
an elongated catheter body comprising a distal end and a proximal end; the elongated catheter body having a longitudinal axis;
at least one scoring element positioned at said distal end of the catheter body, wherein said at least one scoring element is expandable from a contracted state when positioned near said catheter body to an expanded state with a larger diameter so that diseased heart valves can be scored and re-opened;
said at least one scoring element comprising at least one pivotable rodlet and at least one spreading element, a free end of the at least one scoring element being capable of scoring diseased heart valves; the at least one scoring and the at least one spreading elements being parallel to the longitudinal axis of the elongated catheter body when in the contracted state;

wherein said at least one pivotable rodlet is hinged in its middle part at a proximal end of at least one spread rodlet extending in a longitudinal direction of said at least one scoring element in the contracted state; said at least one pivotable rodlet having a cutting edge at its free end;

wherein a proximal end of said at least one pivotable rodlet is movable in the longitudinal direction of the at least one scoring element relative to a distal end of said at least one spread rodlet thereby pivoting said pivotable rodlet.

2. A catheter as claimed in claim 1, wherein multiple cutting edges are arranged in parallel with and/or in any other direction relative to a longitudinal extension of said at least one scoring element.

3. A catheter as claimed in claim 1, wherein at least a portion of said at least one scoring element has a triangular, quadrangular, trapezoidal, pentagonal, hexangular, or multi-angular profile.

4. A catheter as claimed in claim 1, wherein at least a portion of said at least one scoring element has a rounded profile.

5. A catheter as claimed in claim 1, wherein at least a portion of said at least one scoring element has a saw-like profile along its longitudinal cross-section.

6. A catheter as claimed in claim 1, wherein said at least one scoring element comprises at least one scoring band.

7. A catheter as claimed in claim 1, wherein said at least one scoring element comprises a distal end and a proximal end and said distal end of said at least one scoring element is assembled to said distal end of said catheter body and said proximal end of said at least one scoring element is movable.

8. A catheter as claimed in claim 7, wherein said proximal end of said at least one scoring element is fixed to an actuating element.

9. A catheter as claimed in claim 8, wherein said actuating element is a handle.

10. A catheter as claimed in claim 8, wherein said actuating element is a tube movably placed over said catheter body.

11. A catheter as claimed in claim 8, wherein said larger diameter of said at least one scoring element is adjustable by said actuating element.

12. A catheter as claimed in claim 1, wherein at least a portion of said at least one scoring element is covered by a movable sheath.

13. A catheter as claimed in claim 1, wherein said at least one scoring element is made of a metal, a metal alloy, a plastic material, a polymer, a ceramic, or any combination of these materials.

14. A catheter as claimed in claim 13, wherein said at least one scoring element is made of Nitinol, stainless steel or cobalt chromium.

15. A catheter as claimed in claim 1, wherein at least a portion of said at least one scoring element is modifiable by a heat, radiation or chemical source.

16. A catheter as claimed in claim 15, wherein said at least one scoring element is capable of being heated by RF induction heating.

17. A catheter as claimed in claim 1, wherein said at least one scoring element is at least partly coated or is capable of delivering drugs or compounds.

18. A catheter as claimed in claim 17, wherein said drugs prevent or reduce adverse and inflammatory effects and/or the restenosis of said diseased heart valves.

19. A catheter as claimed in claim 1, wherein at least a portion of said at least one scoring element extends in a direction parallel to and/or at an angle to that of the longitudinal axis of said catheter.

20. A catheter as claimed in claim 1, wherein said at least one scoring element comprises an expandable cage structure.

21. A catheter as claimed in claim 1, wherein said at least one scoring element comprises at least one marker to indicate its diameter.

22. A catheter as claimed in claim 21, wherein said marker is made of a radio-opaque material.

23. A catheter as claimed in claim 1, wherein several pivotable rodlets are spaced apart from each other equally on the perimeter of the scoring element, so that they radiate from the catheter body in the expanded state of the scoring element.

24. A catheter as claimed in claim 23, wherein a spread rodlet is assigned to each of said several pivotable rodlets, the spread rodlets being blanked from a metal sheet or cut out from a metal tube.

25. A catheter as claimed in claim 24, wherein said spread rodlets are connected by a connecting element.

26. A catheter as claimed in claim 25, wherein said spread rodlets and said connecting element are formed integrally as one piece.

27. A catheter as claimed in claim 1, wherein the proximal end of each spread rodlet is shaped like a "U" with two brackets and a corresponding pivotable rodlet is hinged between the two brackets of the "U".

* * * * *